United States Patent [19]
Schwark et al.

[11] Patent Number: 6,025,349
[45] Date of Patent: Feb. 15, 2000

[54] PHENYL.-SUBSTITUTED ALKENYLCARBOGUANIDIDES CARRYING PERFLUOROALKYL GROUPS, A PROCESS FOR THEIR PREPARATION, THEIR USE AS A MEDICAMENT OR DIAGNOSTIC AGENT, AND ALSO A MEDICAMENT CONTAINING THEM

[75] Inventors: Jan-Robert Schwark, Frankfurt; Heinz-Werner Kleemann, Bischofsheim; Hans-Jochen Lang, Hofheim; Andreas Weichert, Egelsbach; Wolfgang Scholz, Eschborn; Udo Albus, Florstadt, all of Germany

[73] Assignee: Hoechst Aktiengesellschaft, Frankfurt am Main, Germany

[21] Appl. No.: 09/118,914

[22] Filed: Jul. 20, 1998

Related U.S. Application Data

[63] Continuation of application No. 08/946,886, Oct. 8, 1997, abandoned, which is a continuation of application No. 08/476,867, Jun. 7, 1995, abandoned.

[30] Foreign Application Priority Data

Jun. 20, 1994 [DE] Germany ............................ 44 21 536

[51] Int. Cl.[7] ..................... A61K 31/165; C07C 233/64
[52] U.S. Cl. ..................... 514/182; 514/622; 514/821; 514/921; 564/170; 564/182
[58] Field of Search ..................... 564/182, 170; 514/617, 821, 622, 921

[56] References Cited

U.S. PATENT DOCUMENTS

| | | | |
|---|---|---|---|
| 3,634,508 | 1/1972 | Bream et al. | 260/558 R |
| 3,780,027 | 12/1973 | Cragoe, Jr. et al. | 265/239.6 |
| 4,041,071 | 8/1977 | Grivsky | 260/558 R |
| 4,101,675 | 7/1978 | Panneman | 424/326 |
| 4,318,915 | 3/1982 | Cohnen et al. | 424/273 R |
| 4,544,670 | 10/1985 | Studt et al. | 514/617 |
| 5,578,708 | 11/1996 | Okazaki et al. | 530/399 |
| 5,679,712 | 10/1997 | Schwark et al. | 514/621 |

FOREIGN PATENT DOCUMENTS

| | | |
|---|---|---|
| 0 612 723 | 8/1994 | European Pat. Off. . |
| 612723 | 8/1994 | European Pat. Off. . |
| 628543 | 12/1994 | European Pat. Off. . |
| WO 84/00875 | 3/1984 | WIPO . |

OTHER PUBLICATIONS

Bream et al.: Chem Abst. 84:12322, 1976.
Duff et al., "Amiloride—Antiarrhythmic and Electrophysiologic Actions in Patients With Inducible Sustained Ventricular Tachycardia", Circulation, 79(6):1257–1263, 1989.
European Heart J., 9 (Suppl. 1), 167 (1988) Book of Abstracts.

*Primary Examiner*—Peter O'Sullivan
*Attorney, Agent, or Firm*—Finnegan, Henderson, Farabow, Garrett & Dunner, L.L.P.

[57] ABSTRACT

Phenyl-substituted alkenylcarboguanidides carrying perfluoroalkyl groups, a process for their preparation, their use as a medicament or diagnostic agent, and also a medicament containing them.

Phenyl-substituted alkenylcarboguanidides carrying perfluoroalkyl groups, of the formula I

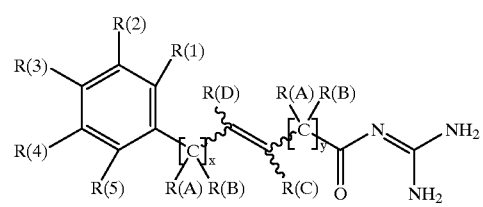

in which the substituents have the meanings stated in the description, and their pharmaceutically suitable salts, are described. They are obtained by reacting a compound II

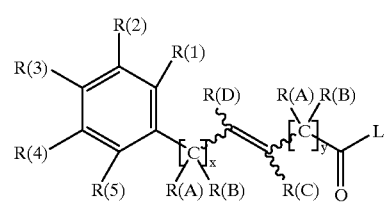

with guanidine, in which R(1) to R(5) and R(A), R(B), R(C) and R(D) have the stated meaning, and L is a leaving group which easily undergoes nucleophilic substitution. Compounds I are excellent cardiovascular therapeutic agents.

20 Claims, No Drawings

PHENYL.-SUBSTITUTED ALKENYLCARBOGUANIDIDES CARRYING PERFLUOROALKYL GROUPS, A PROCESS FOR THEIR PREPARATION, THEIR USE AS A MEDICAMENT OR DIAGNOSTIC AGENT, AND ALSO A MEDICAMENT CONTAINING THEM

This is a continuation of application Ser. No. 08/946,886 filed Oct. 8. 1997, now abandoned, which is a continuation of application Ser. No. 08/476,867 filed Jun. 7. 1995, now abandoned, all of which are incorporated herein by reference.

Phenyl-substituted alkenylcarboguanidides carrying perfluoroalkyl groups, a process for their preparation, their use as a medicament or diagnostic agent, and also a medicament containing them.

The invention relates to phenyl-substituted alkenylcarboguanidides carrying perfluoroalkyl groups, of the formula I

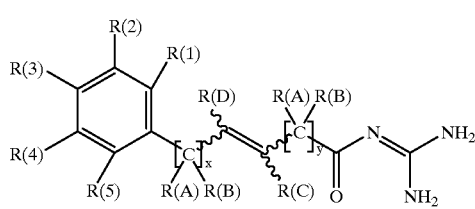

in which R(A) is hydrogen, F, Cl, Br, I, CN, OH, OR(6), $(C_1-C_8)$-alkyl, $O_r(CH_2)_aC_bF_{2b+1}$, $(C_3-C_8)$-cycloalkyl or NR(7)R(8);

r is zero or 1;

a is zero, 1, 2, 3 or 4;

b is 1, 2, 3, 4, 5, 6, 7 or 8;

R(6) is $(C_1-C_8)$-alkyl, $(C_1-C_4)$-perfluoroalkyl, $(C_3-C_8)$-alkenyl, $(C_3-C_8)$-cycloalkyl, phenyl or benzyl;
  where the aromatic radicals are unsubstituted or substituted by 1–3 substituents from the group consisting of F, Cl, $CF_3$, methyl, methoxy and NR(9)R(10);
  R(9) and R(10) are H, $(C_1-C_4)$-alkyl or $(C_1-C_4)$-perfluoroalkyl;

R(7) and R(8) are defined independently of one another as R(6); or

R(7) and R(8) together are 4 or 5 methylene groups, of which one $CH_2$ group can be replaced by oxygen, sulfur, NH, N—$CH_3$ or N-benzyl;

R(B) is independently defined as R(A);

X is zero, 1 or 2;

Y is zero, 1 or 2;

R(C) is hydrogen, F, Cl, Br, I, CN, OR(12), $(C_1-C_8)$-alkyl, $O_p(CH_2)_fC_gF_{2g+1}$ or $(C_3-C_8)$-cycloalkyl;

p is zero or 1;

f is zero, 1, 2, 3 or 4;

g is 1, 2, 3, 4, 5, 6, 7 or 8;

R(12) is $(C_1-C_8)$-alkyl, $(C_1-C_4)$-perfluoroalkyl, $(C_3-C_8)$-alkenyl, $(C_3-C_8)$-cycloalkyl, phenyl or benzyl;
  where the aromatic radicals phenyl or benzyl are unsubstituted or substituted by 1–3 substituents from the group consisting of F, Cl, $CF_3$, methyl, methoxy and NR(13)R(14);
  R(13) and R(14) are, independently of one another, H, $(C_1-C_4)$-alkyl or $(C_1-C_4)$-perfluoroalkyl;

R(D) is defined independently as R(C),

R(1) is hydrogen, $(C_1-C_8)$-alkyl, —$O_t(CH_2)_dC_eF_{2e+1}$, $(C_3-C_8)$-cycloalkyl, F, Cl, Br, I or CN;

t is zero or 1;

d is zero, 1, 2, 3 or 4;

e is 1, 2, 3, 4, 5, 6, 7 or 8;

R(2), R(3), R(4) and R(5) are defined independently of one another as R(1);

but with the condition that at least one of the substituents R(A), R(B), R(C), R(D), R(1), R(2), R(4) or R(5) is a $O_r(CH_2)_aC_bF_{2b+1}$, $O_p(CH_2)_fC_gF_{2g+1}$ or $O_t(CH_2)_dC_eF_{2e+1}$ group and R(3) is not a $O_t(CH_2)_dC_eF_{2e+1}$ group;

as well as the pharmaceutically suitable salts thereof.

Preferred compounds of the formula I are those in which

R(A) is hydrogen, F, Cl, Br, I, CN, OH, OR(6), $(C_1-C_8)$-alkyl, $C_bF_{2b+1}$, $(C_3-C_8)$-cycloalkyl or NR(7)R(8);

b is 1, 2, 3, 4, 5, 6, 7 or 8;

R(6) is $(C_1-C_8)$-alkyl, $(C_1-C_4)$-perfluoroalkyl, phenyl or benzyl;
  where the aromatic radicals phenyl or benzyl are unsubstituted or substituted by 1–3 substituents from the group consisting of F, Cl, $CF_3$, methyl, methoxy and NR(9)R(10);
  R(9) and R(10) are, independently of one another, H, $(C_1-C_4)$-alkyl or $(C_1-C_4)$-perfluoroalkyl;

R(7) and R(8) are defined independently of one another as R(6); or

R(7) and R(8) together are 4 or 5 methylene groups, of which one $CH_2$ group can be replaced by oxygen, sulfur, NH, N—$CH_3$ or N-benzyl;

R(B) is defined independently as R(A);

X is zero or 1;

Y is zero or 1;

R(C) is hydrogen, F, Cl, Br, I, CN, OR(12), $(C_1-C_8)$-alkyl, $C_gF_{2g+1}$;

g is 1, 2, 3, 4, 5, 6, 7 or 8;

R(12) is $(C_1-C_8)$-alkyl, $(C_1-C_4)$-perfluoroalkyl, phenyl or benzyl,
  where the aromatic radicals phenyl or benzyl are unsubstituted or substituted by 1–3 substituents from the group consisting of F, Cl, $CF_3$, methyl, methoxy and NR(13)R(14);
  R(13) and R(14) are, independently of one another, H, $CH_3$ or $CF_3$;

R(D) is defined independently as R(C);

R(1) is hydrogen, $(C_1-C_8)$-alkyl, $C_eF_{2e+1}$, $(C_3-C_8)$-cycloalkyl, F, Cl, Br, I or CN;

e is 1, 2, 3, 4, 5, 6, 7 or 8;

R(2), R(3), R(4) and R(5) are defined independently of one another as R(1);

but with the condition that at least one of the substituents R(A), R(B), R(C), R(D), R(1), R(2), R(4) or R(5) is a $C_bF_{2b+1}$, $C_gF_{2g+1}$ or $C_eF_{2e+1}$ group and R(3) is not a $C_eF_{2e+1}$ group;

as well as the pharmaceutically suitable salts thereof.

Particularly preferred compounds of the formula I are those in which

X is zero;

Y is zero;

R(C) is hydrogen, F, Cl, Br, I, CN, $(C_1-C_8)$-alkyl, $C_gF_{2g+1}$;

g is 1, 2, 3, 4, 5, 6, 7 or 8;

R(D) is defined independently as R(C);

R(1) is hydrogen, $(C_1-C_4)$-alkyl, $C_eF_{2e+1}$, $(C_3-C_8)$-cycloalkyl, F, Cl, Br, I or CN;

e is 1, 2, 3 or 4;

R(2), R(3), R(4) and R(5) are defined independently of one another as R(1);
but with the condition that at least one of the substituents R(C), R (D), R (1), R (2), R (4) or R (5) is a $C_gF_{2g+1}$ or $C_eF_{2e+1}$ group and R(3) is not a $C_eF_{2e+1}$ group;
as well as the pharmaceutically suitable salts thereof.

If the compound of the formula I contains one or more centers of asymmetry, these can have either the S or the R configuration. The compounds may be in the form of optical isomers, of diastereomers, of racemates or of mixtures thereof.

The double-bond geometry of the compounds of the formula I may be either E or Z. The compounds may be in the form of a mixture of double-bond isomers.

The defined alkyl and perfluoroalkyl radicals may be either straight-chain or branched.

The invention furthermore relates to a process for the preparation of the compound I, which comprises
reacting compounds of the formula II

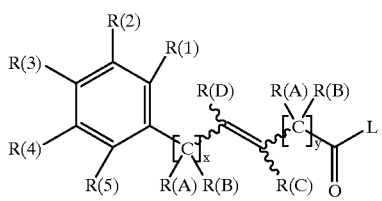

with guanidine, in which R(1) to R(5) and R(A), R(B), R(C) and R(D) have the stated meaning, and L is a leaving group which easily undergoes nucleophilic substitution.

The activated acid derivatives of the formula II in which L is an alkoxy, preferably a methoxy, group, a phenoxy group, phenylthio, methylthio, 2-pyridylthio group, a nitrogen heterocycle, preferably 1-imidazolyl, are advantageously obtained in a manner known per se from the underlying carbonyl chlorides (formula II, L=Cl), which in their turn can again be prepared in a manner known per se from the underlying carboxylic acids (formula II, L=OH), for example with thionyl chloride.

Besides the carbonyl chlorides of the formula II (L=Cl), other activated acid derivatives of the formula II can also be prepared in a manner known per se directly from the underlying benzoic acid derivatives (formula II, L=OH), such as, for example, the methyl esters of the formula II with L=OCH$_3$ by treatment with gaseous HCl in methanol, the imidazolides of the formula II by treatment with carbonyldiimidazole [L=1-imidazolyl, Staab, Angew. Chem. Int. Ed. Engl. 1, 351–367 (1962)], the mixed anhydrides II with Cl—COOC$_2$H$_5$ or tosyl chloride in the presence of triethylamine in an inert solvent, as well as the activations of benzoic acids with dicyclohexylcarbodiimide (DCC) or with O-[(cyano (ethoxy-carbonyl)methylene)amino]-1,1,3,3-tetramethyluronium tetrafluoroborate ("TOTU") [Proceedings of the 21st European Peptide Symposium, Peptides 1990, Editors E. Giralt and D. Andreu, Escom, Leiden 1991]. A number of suitable methods for preparing activated carboxylic acid derivatives of the formula II are indicated, stating source literature, in J. March, Advanced Organic Chemistry, Third Edition (John Wiley & Sons, 1985), page 350.

The reaction of an activated carboxylic acid derivative of the formula II with guanidine takes place in a manner known per se in a protic or aprotic polar but inert organic solvent. In this connection, for the reaction of the methyl carboxylate (II, L=OMe) with guanidine, methanol, isopropanol or THF from 20° C. to the boiling point of these solvents have proved suitable. Most of the reactions of compounds II with salt-free guanidine have advantageously been carried out in aprotic inert solvents such as THF, dimethoxyethane, dioxane. However, water can also be used, with use of a base such as, for example, NaOH, as solvent for the reaction of II with guanidine. When L is Cl, it is advantageous to add an acid scavenger, for example in the form of excess guanidine, to bind the hydrohalic acid.

Some of the underlying carboxylic acid derivatives of the formula II are known and described in the literature. The unknown compounds of the formula II can be prepared by methods known from the literature. The resulting alkenylcarboxylic acids are reacted by one of the process variants described above to give compounds I according to the invention.

The introduction of some substituents takes place by methods known from the literature for palladium-mediated cross-coupling of aryl halides or aryl triflates with, for example, organostannanes, organoboronic acids or organoboranes or organocopper or organozinc compounds.

Carbonylguanidines I are generally weak bases and can bind acid to form salts. Suitable acid addition salts are salts of all pharmacologically suitable acids, for example halides, especially hydrochlorides, lactates, sulfates, citrates, tartrates, acetates, phosphates, methylsulfonates, p-toluenesulfonates.

The compounds I are substituted acylguanidines. The most prominent representative of the acylguanidines is the pyrazine derivative amiloride, which is used in therapy as potassium-sparing diuretic. Numerous other compounds of the amiloride type are described in the literature, such as, for example, dimethylamiloride or ethylisopropylamiloride.

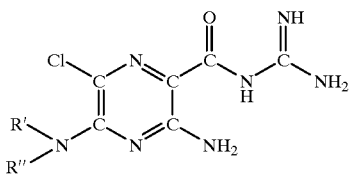

Amiloride: R', R"=H
Dimethylamiloride; R', R"=CH$_3$
Ethylisopropylamiloride: R'=C$_2$H$_5$, R"=CH(CH$_3$)$_2$ In addition, investigations indicating antiarrhythmic properties of amiloride have been published [Circulation 79, 1257–63 (1989)]. However, widespread use as antiarrhythmic agent is prevented by the fact that this effect is only weak and occurs accompanied by a blood pressure-lowering and saluretic effect, and these side effects are undesired in the treatment of cardiac rhythm disturbances.

Indications of antiarrhythmic properties of amiloride have also been obtained in experiments on isolated animal hearts [Eur. Heart J. 9 (suppl. 1): 167 (1988) book of abstracts]. Thus, for example, it has been found on rat hearts that it was possible completely to suppress artificially induced ventricular fibrillation by amiloride. Even more potent than amiloride in this model was the amiloride derivative ethylisopropylamiloride mentioned above.

The PCT publication Wo 84 00875 relates to guanidine compounds which may also contain benzoyl groups, but a CH$_2$ group is always present between the benzoyl group and the guanidine moiety of the molecule, and there is no case of benzoylguanidines of the structure according to the invention. These known compounds are used for treating infections derived from protozoa.

U.S. Pat. No. 3,780,027 claims acylguanidines which are structurally similar to the compounds of the formula I and are derived from commercially available loop diuretics such as bumetanide. Correspondingly, these compounds are reported to have a potent salidiuretic activity.

It was therefore surprising that the compounds according to the invention have no unwanted and disadvantageous salidiuretic properties but have very good antiarrhythmic properties; they are therefore well suited for the treatment of conditions such as occur, for example, in manifestations of oxygen deficiency. The compounds are, as a consequence of their pharmacological properties, outstandingly suitable as antiarrhythmic pharmaceuticals with cardioprotective component for infarct prophylaxis and infarct treatment and for the treatment of angina pectoris, in which case they also preventively inhibit or greatly reduce the pathophysiological processes in the development of ischemia-induced damage, especially in the induction of ischemia-induced cardiac arrhythmias. Because of their protective effects against pathological hypoxic and ischemic situations, the compounds of the formula I according to the invention can, as a consequence of inhibition of the cellular $Na^+/H^+$ exchange mechanism, be used as pharmaceuticals for the treatment of all acute or chronic ischemia-induced damage or diseases induced primarily or secondarily thereby. This relates to their use as pharmaceuticals for surgical interventions, for example in organ transplants, in which case the compounds can be used both to protect the organs in the donor before and during removal, to protect removed organs, for example on treatment with or storage thereof in physiological bath liquids, as well as on transfer into the recipient organism. The compounds are likewise valuable pharmaceuticals with a protective action when performing angioplastic surgical interventions, for example on the heart as well as on peripheral vessels. In accordance with their protective effect on ischemia-induced damage, the compounds are also suitable as pharmaceuticals for the treatment of ischemias of the nervous system, especially of the CNS, in which case they are suitable, for example, for the treatment of stroke or cerebral edema. Furthermore, the compounds of the formula I according to the invention are likewise suitable for the treatment of types of shock, such as, for example, allergic, cardiogenic, hypovolemic and bacterial shock.

Furthermore, the compounds of the formula I according to the invention are distinguished by a potent inhibitory effect on the proliferation of cells, for example fibroblast cell proliferation and proliferation of smooth vascular muscle cells. The compounds of the formula I are therefore suitable as valuable therapeutics for diseases in which cell proliferation represents a primary or secondary cause, and can therefore be used as antiatherosclerotics, agents to prevent late complications of diabetes, cancers, fibrotic disorders such as pulmonary fibrosis, hepatic fibrosis or renal fibrosis, organ hypertrophies and hyperplasias, especially for prostate hyperplasia and prostate hypertrophy.

The compounds according to the invention are effective inhibitors of the cellular sodium/proton antiporter ($Na^+/H^+$ exchanger) which is elevated in a large number of disorders (essential hypertension, atherosclerosis, diabetes etc), even in those cells which are easily amenable to measurements, such as, for example, in erythrocytes, platelets or leukocytes. The compounds according to the invention are therefore suitable as excellent and simple scientific tools, for example in their use as diagnostic agents for the determination and differentiation of certain types of hypertension, but also atherosclerosis, diabetes, proliferative disorders etc. In addition, the compounds of the formula I are suitable for preventive therapy to prevent the genesis of high blood pressure, for example essential hypertension.

Pharmaceuticals which contain a compound I can moreover be administered orally, parenterally, intravenously, rectally or by inhalation, the preferred administration depending on the particular course of the disorder. The compounds I can moreover be used alone or together with pharmaceutical ancillary substances, both in veterinary and in human medicine.

The particular ancillary substances suitable for the required pharmaceutical formulation are familiar to the skilled worker on the basis of his expert knowledge. Besides solvents, gel formers, suppository bases, tablets auxiliaries and other active substance vehicles, it is possible to use, for example, antioxidants, dispersants, emulsifiers, antifoam agents, masking flavors, preservatives, solubilizers or colorants.

For a form for oral use, the active compounds are mixed with the additives suitable for this purpose, such as excipients, stabilizers or inert diluents, and converted by conventional methods into the suitable dosage forms such as tablets, coated tablets, hard gelatin capsules, aqueous, alcoholic or oily solutions. Examples of inert vehicles which can be used are gum arabic, magnesia, magnesium carbonate, potassium phosphate, lactose, glucose or starch, especially corn starch. This preparation can take place either as dry or as wet granules. Examples of suitable oily excipients or solvents are vegetable or animal oils, such as sunflower oil or fish liver oil.

For subcutaneous or intravenous administration, the active compounds are converted, if required with the substances customary for this purpose, such as solubilizers, emulsifiers or other ancillary substances, into solution, suspension or emulsion. Examples of suitable solvents are: water, physiological saline solution or alcohols, for example ethanol, propanol, glycerol, but also sugar solutions such as glucose or mannitol solutions, or else a mixture of the various solvents mentioned.

Examples of suitable pharmaceutical formulations for administration in the form of aerosols or sprays are solutions, suspensions or emulsions of the active substance of the formula I in a pharmaceutically acceptable solvent such as, in particular, ethanol or water, or a mixture of such solvents.

The formulation can, if required, also contain other pharmaceutical ancillary substances such as surfactants, emulsifiers and stabilizers, and a propellant gas. A preparation of this type normally contains the active substance in a concentration of about 0.1 to 10, in particular about 0.3 to 3% by weight.

The dosage of the active substance of the formula I to be administered, and the frequency of administration, depend on the potency and duration of action of the compounds used; in addition also on the nature and severity of the disease to be treated and on the sex, age, weight and individual response of the mammal to be treated. On average, the daily dose of a compound of the formula I for a patient weighing about 75 kg is at least 0.001 mg/kg, preferably 0.01 mg/kg, to a maximum of 10 mg/kg, preferably. 1 mg/kg of body weight. For acute episodes of the disease, for example immediately after suffering a myocardial infarct, even higher and, in particular, more frequent dosages may also be necessary, for example up to 4 individual doses a day. Up to 200 mg per day may be necessary in particular on i.v. use, for example for an infarct patient in intensive care.

List of abbrevations:

| | |
|---|---|
| MeOH | Methanol |
| DMF | N,N-Dimethylformamide |
| EI | Electron Impact |
| DCI | Desorption-Chemical Ionization |
| RT | Room Temperature |
| EA | Ethyl acetate (EtOAc) |
| mp | Melting point |
| HEP | n-Heptane |
| DME | Dimethoxyethane |
| ES | Electrospray ionization |
| FAB | Fast Atom Bombardment |
| $CH_2Cl_2$ | Dichloromethane |
| THF | Tetrahydrofuran |
| eq. | equivalent |

Experimental part
General methods for the preparation of alkenylcarbonyl-guanidines (I)

Variant A: from alkenylcarboxylic acids (II, L=OH) 1.0 eq. of the carboxylic acid derivative of the formula II is dissolved or suspended in anhydrous THF (5 ml/mmol) and then 1.1 eq. of carbonyldiimidazole are added. After stirring at RT for 2 hours, 5.0 eq. of guanidine are introduced into the reaction solution. After stirring overnight, the THF is removed by distillation under reduced pressure (rotary evaporator), water is added, the pH is adjusted to 6 to 7 with 2N HCl, and the corresponding guanidide (formula I) is filtered off. The carbonyl-guanidines obtained in this way can be converted by treatment with aqueous, methanolic or ethereal hydrochloric acid or other pharmacologically suitable acids into the corresponding salts.

Variant B: from alkyl alkenylcarboxylates (II, L=O-alkyl)

1.0 eq. of the alkyl carboxylate of the formula II and 5.0 eq. of guanidine (free base) are dissolved in isopropanol or suspended in THF and heated to reflux until reaction is complete (thin-layer check) (typical reaction time 2 to 5 h). The solvent is removed by distillation under reduced pressure (rotary evaporator), the residue is taken up in EA, and this solution is washed and 3x with $NaHCO_3$ solution. It is dried over $Na_2SO_{4}$, the solvent is removed by distillation in vacuo, and the product is chromatographed on silica gel with a suitable mobile phase, for example EA/MeOH 5:1.
(For salt formation, see variant A)

EXAMPLE 1

Meta-Trifluoromethylcinnamic Acid Guanidide Hydrochloride was prepared by variant A starting from meta-trifluoromethylcinnamic acid.
Colorless crystals
mp 182–190° C.

EXAMPLE 2

Ortho-Trifluoromethylcinnamic Acid Guanidide Hydrochloride was prepared by variant A starting from ortho-trifluoromethylcinnamic acid.
Colorless crystals
mp 185–200° C.

EXAMPLE 3

Trans-2-Methyl-3-(3-Trifluoromethylphenyl)-Acrylic Acid Guanidide 3 a) 1 eq. of triethyl 2-phosphonopropionate was deprotonated with 1 eq. of n-butyllithium in hexane at 0° C. and subsequently, at RT, 1 eq. of trifluoromethylbenzaldehyde was added. After the aldehyde had reacted completely, workup was carried out with water, extracting by shaking three times with toluene. The combined organic phases were dried over magnesium sulfate and then the solvent was removed in vacuo and the remaining crude product was chromatographed on silica gel with EA/HEP mixtures as eluent. Ethyl trans-2-methyl-3-(3-trifluoromethylphenyl)-acrylate was isolated (<3% cis isomer as impurity).

3 b) The ester from 3 a) was converted by variant B to trans-2-methyl-3-(3-trifluoromethylphenyl)acrylic acid guanidide.
MS: 272 $(M+1)^+$
mp 124–126° C.

EXAMPLE 4

Trans-2-Methyl-3-[3,5-Bis(Trifluoromethyl)Phenyl] Acrylic Acid Guanidide Hydrochloride was prepared in analogy to Example 3 from 3,5-bis (trifluoromethyl)benzaldehyde.
MS: 340 $(M+1)^+$
mp 56–58° C.

EXAMPLE 5

Trans-2-Methyl-3-[2-Fluoro-5-Trifluoromethylphenyl]Lacrylic Acid Guanidide was prepared in analogy to Example 3 from 2-fluoro-5-trifluoromethylbenzaldehyde.
MS: 290 $(M+1)^+$
mp 139° C.

EXAMPLE 6

Trans-2-Methyl-3-[2-Chloro-5-Trifluoromethylphenyl]Acrylic Acid Guanidide was prepared in analogy to Example 3 from 2-chloro-5-trifluoromethylbenzaldehyde.
MS: 306 $(M+1)^+$
mp 124–132° C.

EXAMPLE 7

Trans-2-Methyl-3-[3-Fluoro-5-Trifluoromethylphenyl]Acrylic Acid Guanidide was prepared in analogy to Example 3 from 3-fluoro-5-trifluoromethylbenzaldehyde.
MS: 290 $(M+1)^+$
mp 132° C.

EXAMPLE 8

Trans-2-Methyl-3-[2-Fluoro-6-Trifluoromethylphenyl]Acrylic Acid Guanidide Hydrochloride was prepared in analogy to Example 3 from 2-fluoro-6 -mp 95° C.

EXAMPLE 9

Trans-2-Methyl-3-[2-Trifluoromethyl-Phenyl] Acrylic Acid Guanidide was prepared in analogy to Example 3 from 2-trifluoromethylbenzaldehyde.
MS: 272 (M +1)+
mp 124–130° C.

EXAMPLE 10

Trans-2,3-Dimethyl-3-[2-Fluoro-5-Trifluoromethyl-Phenyl]-Acrylic Acid Guanidide was prepared in analogy to Example 3 from 2-fluoro-5-trifluoromethylacetophenone.

MS: 304 (M+1)$^+$
mp 189° C.

EXAMPLE 11

Cis-2,3-Diemethyl-3-[2-Fluoro-5-Trifluoromethyl-Phenyl]-Acrylic Acid Guanidide
was prepared in analogy to Example 3 from 2-fluoro-5-trifluoromethyl-acetophenone.
MS: 304 (M+1)$^+$
mp 140° C.

EXAMPLE 12

Trans-2,3-Dimethyl-3-[3-Trifluoromethyl-Phenyl]-Acrylic Acid Guanidide
was prepared in analogy to Example 3 from 2-fluoro-5-trifluoromethyl-acetophenone.
MS: 266 (M+1)$^+$
mp 129° C.

EXAMPLE 13

Trans-2-Methyl-3-Trifluoromethyl-3-[3-Trifluoromethyl-Phenyl]-Acrylic Acid Guanidide
prepared in analogy to Example 3 from ωωω-trifluoromethyl-3-trifluoromethyl-acetophenone.
MS: 340 (M+1)$^+$
mp 63° C.

EXAMPLE 14

Trans-2-Trifluoromethyl-3-Phenyl-Acrylic Acid Guanidide
was prepared by variant A from cis-2-trifluoromethylcinnamic acid (prepared by processes disclosed in the literature).
MS: 258 (M+1)$^+$
amorphous
Pharmacological data
Inhibition of the Na$^+$/H$^+$ exchanger of rabbit erythrocytes:
White New Zealand rabbits (Ivanovas) received a standard diet containing 2% cholesterol for six weeks in order to activate Na$^+$/H$^+$ exchange and thus to be able to determine the Na$^+$ influx into the erythrocytes via Na$^+$/H$^+$ exchange by flame photometry. The blood was taken from the ear arteries and anticoagulated by 25 IU/ml potassium heparin. A portion of each sample was used for duplicate determination of the hematocrit by centrifugation. Aliquots each of 100 μl were used to measure the initial Na$^+$ content of the erythrocytes.

In order to determine the amiloride-sensitive sodium influx, 100 μl of each blood sample were incubated in each case in 5 ml of a hyperosmolar salt/sucrose medium (mmol/l: 140 NaCl, 3 KCl, 150 sucrose, 0.1 ouabain, 20 tris-hydroxymethylaminomethane) at pH 7.4 and 37° C. The erythrocytes were then washed three times with ice-cold MgCl$_2$/ouabain solution (mmol/l: 112 MgCl$_2$, 0.1 ouabain) and hemolyzed in 2.0 ml of distilled water. The intracellular sodium content was determined by flame photometry.

The net Na$^+$ influx was calculated from the difference between the initial sodium levels and the sodium content of the erythrocytes after incubation. The sodium influx which can be inhibited by amiloride was found from the difference in the sodium content of the erythrocytes after incubation with and without amiloride 3×10$^{-4}$ mol/l. The compounds according to the invention were also subjected to this process.

Results on the inhibition of the Na$^+$/H$^+$ exchanger:
Example (see exp. part) IC$_{50}$ (μmol)

| Example (see exp. part) | IC$_{50}$ (μmol) |
|---|---|
| 1 | <1 |
| 3 | <1 |
| 10 | <1 |

EXAMPLE 15

Z-2-Fluoro-3-(2-Fluoro-5-Trifluoromethylphenyl) Propenoic Acid Guanidine Hydrochloride

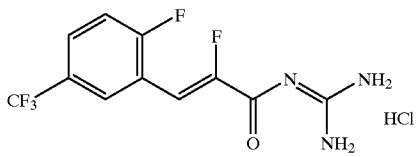

15a) Z-2-Fluoro-3-(2-fluoro-5-trifluoromethyl-phenyl) propenoic acid methylester was prepared in analogy to example 3 from triethyl-2-fluoro-2-phosphonate and 2-fluoro-5-trifluoromethyl-benzaldehyde. The E/Z-isomers were separated by chromatography on silicagel.

15b) The Z-ester was transformed into the acid under standard conditions (sodiumhydroxide/methanol).

15c) The Z-2-fluoro-3-(2-fluoro-5-trifluormethyl-phenyl) propenoic acid was transformed into the guanidin derivative in analogy to procedure A.
MS: 294 (m+1)$^+$
mp: 185° C. (free base, hydrochloride amorph)

We claim:
1. A phenyl-substituted alkenylcarboguanidide carrying perfluoroalkyl groups, of the formula I

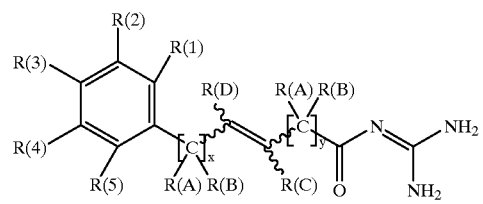

in which
R(A) is hydrogen, F, Cl, Br, I, CN, OH, OR(6), (C$_1$–C$_8$)-alkyl, O$_r$(CH$_2$)$_a$C$_b$F$_{2b+1}$, (C$_3$–C$_8$)-cyclo-alkyl or NR(7)R(8);
r is zero or 1;
a is zero, 1, 2, 3 or 4;
b is 1, 2, 3, 4, 5, 6, 7 or 8;
R(6) is (C$_1$–C$_8$)-alkyl, (C$_1$–C$_4$)-perfluoroalkyl, (C$_3$–C$_8$)-alkenyl, (C$_3$–C$_8$)-cycloalkyl, phenyl or benzyl,
where the aromatic radicals phenyl or benzyl are unsubstituted or substituted by 1–3 substituents from the group consisting of F, Cl, CF$_3$, methyl, methoxy and NR(9)R(10);
R(9) and R(10) are, independently of one another, H, (C$_1$–C$_4$)-alkyl or (C$_1$–C$_4$)-perfluoroalkyl;
R(7) and R(8) are defined independently of one another as R(6); or R(7) and R(8) together are 4 or 5 methylene groups, of which one $CH_2$ group can be replaced by oxygen, sulfur, NH, N—$CH_3$ or N-benzyl;

R(B) is independently defined as R(A);

X is zero, 1 or 2;

Y is zero, 1 or 2;

R(C) is hydrogen, F, Cl, Br, I, CN, OR(12), $(C_1-C_8)$-alkyl, $O_p(CH_2)_fC_gF_{2g+1}$ or $(C_3-C_8)$-cycloalkyl;

p is zero or 1;

f is zero, 1, 2, 3 or 4;

g is 1, 2, 3, 4, 5, 6, 7 or 8;

R(12) is $(C_1-C8)$-alkyl, $(C_1-C_4)$-perfluoroalkyl, $(C_3-C8)$-alkenyl, $(C_3-C_8)$-cycloalkyl, phenyl or benzyl, where the aromatic radicals phenyl or benzyl are unsubstituted or substituted by 1–3 substituents from the group consisting of F, Cl, $CF_3$, methyl, methoxy and NR(13)R(14);

R(13) and R(14) are independently of one another H, $(C_1-C_4)$-alkyl or $(C_1-C_4)$-perfluoroalkyl;

R(D) is defined independently as R(C);

R(1) is hydrogen, $(C_1-C_8)$-alkyl, $-O_t(CH_2)_dC_eF_{2e+1}$, $(C_3-C_8)$-cycloalkyl, F, Cl, Br, I or CN;

t is zero or 1;

d is zero, 1, 2, 3 or 4;

e is 1, 2, 3, 4, 5, 6, 7 or 8;

R(2), R(3), R(4) and R(5) are defined independently of one another as R(1);

but with the condition that at least one of the substituents R(A), R(B), R(C), R(D), R(1), R(2), R(4) or R(5) is a $O_t(CH_2)_dC_bF_{2b+1}$, $O_p(CH_2)_fC_gF_{2g+1}$ or $O_t(CH_2)_dC_eF_{2e+1}$ group and R(3) is not a $O_t(CH_2)_dC_eF_{2e+1}$ group;

as well as the pharmaceutically suitable salts thereof.

2. A compound of the formal I as claimed in claim 1, in which

R(A) is hydrogen, F, Cl, Br, I, CN, OH, OR(6), $(C_1-C_8)$-alkyl, $C_bF_{2b+1}$, $(C_3-C_8)$-cycloalkyl or NR(7)R(8);

b is 1, 2, 3, 4, 5, 6, 7 or 8;

R(6) is $(C_1-C_8)$-alkyl, $(C_1-C_4)$-perfluoroalkyl, phenyl or benzyl, where the aromatic radicals phenyl or benzyl are unsubstituted or substituted by 1–3 substituents from the group consisting of F, Cl, $CF_3$, methyl, methoxy and NR(9)R(10);

R(9) and R(10) are H, $(C_1-C_4)$-alkyl or $(C_1-C_4)$-perfluoroalkyl;

R(7) and R(8) are defined independently of one another as R(6); or

R(7) and R(8) together are 4 or 5 methylene groups, of which one $CH_2$ group can be replaced by oxygen, sulfur, NH, N—$CH_3$ or N-benzyl;

R(B) is defined independently as R(A);

X is zero or 1;

Y is zero or 1;

R(C) is hydrogen, F, Cl, Br, I, CN, OR(12), $(C_1-C_8)$-alkyl, $C_gF_{2g+1}$;

g is 1, 2, 3, 4, 5, 6, 7 or 8;

R(12) is $(C_1-C_8)$-alkyl, $(C_1-C_4)$-perfluoroalkyl, phenyl or benzyl, where the aromatic radicals phenyl or benzyl are unsubstituted or substituted by 1–3 substituents from the group consisting of F, Cl, $CF_3$, methyl, methoxy and NR(13)R(14);

R(13) and R(14) are independently of one another H, $CH_3$ or $CF_3$;

R(D) is defined independently as R(C),

R(1) is hydrogen, $(C_1-C_8)$-alkyl, $C_eF_{2e+1}$, $(C_3-C_8)$-cycloalkyl, F, Cl, Br, I or CN;

e is 1, 2, 3, 4, 5, 6, 7 or 8;

R(2), R(3), R(4) and R(5) are defined independently of one another as R(1);

but with the condition that at least one of the substituents R(A), R(B), R(C), R(D), R(1), R(2), R(4) or R(5) is a $C_bF_{2b+1}$, $C_gF_{2g+1}$ or $C_eF_{2e+1}$ group and R(3) is not a $C_eF_{2e+1}$ group.

3. A compound of the formula I as claimed in claim 1, in which

X is zero;

Y is zero;

R(C) is hydrogen, F, Cl, Br, I, CN, $(C_1-C_8)$-alkyl, $C_gF_{2g+1}$;

g is 1, 2, 3, 4, 5, 6, 7 or 8;

R(D) is defined independently as R(C);

R(1) is hydrogen, $(C_1-C_4)$-alkyl, $C_eF_{2e+1}$, $(C_3-C_8)$-cycloalkyl, F, Cl, Br, I or CN;

e is 1, 2, 3 or 4;

R(2), R(3), R(4) and R(5) are defined independently of one another as R(1);

but with the condition that at least one of the substituents R(C), R(D), R(1), R(2), R(4) or R(5) is a $C_gF_{2g+1}$ or $C_eF_{2e+1}$ group and R(3) is not a $C_eF_{2e+1}$ group.

4. A process for the preparation of a compound I as claimed in claim 1, which comprises reacting a compound of the formula II

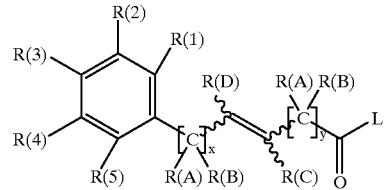

with guanidine, in which R(1) to R(5) and R(A), R(B), R(C) and R(D) have the stated meaning, and L is a leaving group which easily undergoes nucleophilic substitution.

5. A method of treating or preventing arrhythmias, which comprises administering to a host in need of said treatment an effective amount of a compound of formula I or a salt thereof as claimed in claim 1.

6. A method of treating or preventing myocardial infarct, which comprises administering to a host in need of said treatment an effective amount of a compound of formula I or a salt thereof as claimed in claim 1.

7. A method of treating or preventing angina pectoris, which comprises administering to a host in need of said treatment an effective amount of a compound of formula I or a salt thereof as claimed in claim 1.

8. A method of treating or preventing diseases caused by ischemic conditions, which comprises administering to a host in need of said treatment an effective amount of a compound of formula I or a salt thereof as claimed in claim 1.

9. A method of treating or preventing ischemic conditions of the heart, which comprises administering to a host in need of said treatment an effective amount of a compound of formula I or a salt thereof as claimed in claim 1.

10. A method of treating or preventing ischemic conditions of the peripheral and central nervous systems and of stroke, which comprises administering to a host in need of said treatment an effective amount of a compound of formula I or a salt thereof as claimed in claim 1.

11. A method of treating or preventing ischemic conditions of the peripheral organs and limbs, which comprises administering to a host in need of said treatment an effective amount of a compound of formula I or a salt thereof as claimed in claim 1.

12. A method of treating shock conditions, which comprises administering to a host in need of said treatment an effective amount of a compound of formula I or a salt thereof as claimed in claim 1.

13. A pharmaceutical composition for use in surgical operations and organ transplants, which comprises an effective amount of a compound of formula I or a salt thereof as claimed in claim 1 and a pharmaceutically acceptable carrier.

14. A pharmaceutical composition for use in preserving and storing transplants for surgical procedures, which comprises an effective amount of a compound of formula I or a salt thereof as claimed in claim 1 and a pharmaceutically acceptable carrier.

15. A method of treating diseases in which cell proliferation is a primary or secondary cause, which comprises administering to a host in need of said treatment an effective amount of a compound of the formula I or a salt thereof as claimed in claim 1.

16. The method according to claim 15, wherein the disease in which cell proliferation is a primary or secondary cause is atherosclerosis, a late complication of diabetes, a cancer, a fibrotic disease or prostate hyperplasia.

17. The method according to claim 16, wherein the fibrotic disease is pulmonary fibrosis, hepatic fibrosis, or renal fibrosis.

18. A diagnostic agent for inhibiting the Na+/H+ exchanger and for diagnosing hypertension and proliferative diseases, which comprises an effective amount of a compound of formula I or a salt thereof as claimed in claim 1.

19. A pharmaceutical composition for treating (1) arrhythmia, (2) myocardial infarct, (3) angina pectoris, (4) ischemic conditions of (I) the heart, (ii) the peripheral and central nervous systems, (iii) the peripheral organs and limbs, and (iv) stroke, (5) a shock condition, or (6) a disease in which cell proliferation is a primary or secondary cause, for inhibiting the Na+/H+ exchanger, or for diagnosing hypertension, atherosclerosis, diabetes or a proliferative disease, which comprises an effective amount of a compound of formula I or a salt thereof as claimed in claim 1 together with a pharmaceutically acceptable carrier.

20. A pharmaceutical composition for treating diseases caused by ischemic conditions, which comprises an effective amount of a compound of formula I or a salt thereof as claimed in claim 1 together with a pharmaceutically acceptable carrier.

* * * * *

UNITED STATES PATENT AND TRADEMARK OFFICE
CERTIFICATE OF CORRECTION

PATENT NO. : 6,025,349
DATED : February 15, 2000
INVENTOR(S) : Jan-Robert Schwark et al.

It is certified that error appears in the above-identified patent and that said Letters Patent is hereby corrected as shown below:

<u>Title page, Item [54] Title, line 1,</u>
"Phenyl.-Substituted" should read -- Phenyl-Substituted --.

<u>Column 10, claim 1,</u>
Line 52, change "$F_{2b+}1$" to -- $F_{2b+1}$ --;

<u>Column 11, claim 1,</u>
Line 12, change "C8" to -- $C_8$ --;
Line 32, change "R (3)" to -- R(3) --.

<u>Column 11, claim 2,</u>
Line 35, change "formal" to -- formula --.

<u>Column 12, claim 1,</u>
Line 13, change "C8" to -- $C_8$ -- and change "$(C_3-C_8)$ -cycloalkyl" to
-- $(C_3-C_8)$-cycloalkyl --.

Signed and Sealed this

Twenty-sixth Day of March, 2002

Attest:

*Attesting Officer*

JAMES E. ROGAN
*Director of the United States Patent and Trademark Office*